US006968124B1

(12) United States Patent
Varanasi et al.

(10) Patent No.: US 6,968,124 B1
(45) Date of Patent: Nov. 22, 2005

(54) ELECTRIC LIQUID VOLATILE DISPENSER

(75) Inventors: Padma Prabodh Varanasi, Racine, WI (US); Joel E. Adair, Racine, WI (US); Brian T. Davis, Burlington, WI (US); Saleh Adam Saleh, Vernon Hills, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/876,856

(22) Filed: Jun. 25, 2004

(51) Int. Cl.[7] .............................................. F24F 6/00
(52) U.S. Cl. ...................................... 392/392; 392/395
(58) Field of Search ............................... 392/386, 390, 392/391, 392, 394, 395; 122/366, 367.1; 239/34, 44, 45, 53

(56) References Cited

U.S. PATENT DOCUMENTS

| | | | |
|---|---|---|---|
| 4,968,487 A | 11/1990 | Yamamoto et al. | |
| 5,038,394 A | 8/1991 | Hasegawa et al. | |
| 5,095,647 A | 3/1992 | Zobele et al. | |
| 5,222,186 A | 6/1993 | Schimanski et al. | |
| 5,290,546 A | 3/1994 | Hasegawa et al. | |
| 5,647,053 A | 7/1997 | Schroeder et al. | |
| 5,796,914 A | 8/1998 | Gatzemeyer et al. | |
| 5,937,140 A * | 8/1999 | Leonard et al. | 392/392 |
| 6,236,807 B1 * | 5/2001 | Ruffolo et al. | 392/390 |
| 6,278,840 B1 | 8/2001 | Basaganas Millan | |
| 6,361,752 B1 | 3/2002 | Demarest et al. | |
| 6,374,044 B1 | 4/2002 | Freidel | |
| 6,411,776 B1 | 6/2002 | Millan | |
| 6,446,583 B2 | 9/2002 | Vieira | |
| 6,466,739 B2 | 10/2002 | Ambrosi et al. | |
| 6,567,613 B2 | 5/2003 | Rymer | |
| 6,603,924 B2 * | 8/2003 | Brown et al. | 392/390 |
| 6,850,697 B2 * | 2/2005 | Basaganas Millan | 392/390 |
| 2003/0231876 A1 | 12/2003 | Basaganas Millan | |

FOREIGN PATENT DOCUMENTS

FR 2 724 847 3/1996

OTHER PUBLICATIONS

"PTC Thermistor Heating Elements", Appliance Magazine, Nov. 2001.

* cited by examiner

Primary Examiner—Sang Y. Paik (57) ABSTRACT

A plug-in type dispenser of liquid volatiles, such as insecticides, fragrants, and the like, of the type having a heater for evaporating the liquid volatiles from a wick, provides improved volatile dispersion characteristics and in-use indication. Air flow through the dispenser and around the wick is increased, and the outlet is sized and configured to avoid condensation on the inside and outside of the housing as well as to increase the vertical component of the expelled air stream. An internal lamp transmits light to be reflected off of an exterior in-use indicator surface of the housing to provide visual indication that the dispenser is active.

46 Claims, 7 Drawing Sheets

ELECTRIC LIQUID VOLATILE DISPENSER

CROSS-REFERENCE TO RELATED APPLICATIONS

Not applicable.

STATEMENT OF FEDERALLY SPONSORED RESEARCH/DEVELOPMENT

Not applicable.

BACKGROUND OF THE INVENTION

The present invention relates to a dispenser of volatile liquids, and more particularly to a device for evaporating liquid moving up a wick.

Wick-based liquid volatile dispensing systems are known in the art for dispersing vaporized particles of any number of liquids into the air. Such systems are often used in the home with liquids varying from insect repellents to air fresheners. One end of a wick can be submerged in the liquid to be dispersed. The submerged portion of the wick absorbs the liquid, some of which diffuses by capillary or wicking action into the exposed, unsubmerged portion of the wick. The exposed portion of the wick is locally heated, often by means of a ring-shaped heater which fits about the exposed tip of the wick. This causes the liquid which has diffused into the exposed portion of the wick to evaporate into the surrounding air. Continual application of heat to the exposed portion of the wick results in an evaporation process that continues until the liquid is consumed.

The primary difficulty associated with conventional heated wick liquid dispensers is controlling the dispersion of the volatile materials, particularly the rate and distance of dispersion of the volatile materials.

The evaporation rate of the volatile materials must be rapid enough to begin dispersing volatiles shortly after it is activated, and yet provide sustained release over a useful life. The dispersion rate can also vary over time. Upon first activating the dispenser (after the heater reaches operating temperature), the release rate is typically greater than after several hours of use. Therefore, it is difficult to select components and the appropriate amount of liquid to use for a given application.

The evaporated volatile materials usually must emanate through a relatively large air space, for example, one or more rooms of a house. Extremely localized dispersion limits the effect of the volatile to the immediate area around the dispenser. Sometimes, a portion of the evaporated materials becomes trapped inside the housing of the dispenser. This can cause it to condense within the housing, and in severe cases, can result in liquid dripping out of the bottom of the dispenser. Loss of liquid through evaporation when the heater is deactivated is also common. Sometimes condensation of the warm air stream can leave deposits of volatized active materials at the exterior of the housing, particularly at or around the outlet opening. This can be unsightly and leave the deposited material susceptible to contact by the user.

Another problem with electric volatile dispensers pertains to providing a clear indication to the consumer that the device is operating. This includes provides immediate feedback of activation to the consumer even when there is some delay in dispersion of the volatile, as when the heater is warming up to operating temperature. It also helps the consumer know that the device, since activated, may be warm. It can also indicate to the consumer that the device should be unplugged if the liquid has been exhausted.

A light is commonly used to provide an in-use indication. The lamp is powered when the dispenser is plugged into an electrical outlet and thus illuminates only when the dispenser is powered. Sometimes, the dispenser housing has a small translucent window or is partially, or totally, constructed of translucent material so that the light is visible from outside the housing. The opening or translucent area is usually at the top of the dispenser, which is at the height of the electrical outlet, so it can be viewed readily from a person standing nearby. Having a light opening in the housing is problematic because liquids and small objects, fingers for example, can enter there. A separate translucent window adds to assembly and translucent components add to the cost of the product. Another concern relevant to evaporative dispensers is that the lamp is often exposed to the heat source, which makes it apt to burn out more rapidly.

Accordingly, there is a need for a liquid volatile dispenser that better addresses the aforesaid problems.

SUMMARY OF THE INVENTION

The present invention provides an electrically activated dispenser of liquid volatiles, such as insecticides and fragrants, with improved dispersion characteristics and in-use indication.

In one aspect, the dispenser of the present invention includes a housing having an outlet opening and an exterior in-use indicator surface. The housing contains a heater and a lamp, both of which are electrically coupled to an electrical plug mounted to the housing. A container of liquid volatiles can be mounted to the housing proximate the heater to permit evaporation of the liquid volatiles through the outlet opening. When the heater is energized, the lamp transmits light exterior to the housing onto an in-use indicator surface.

In more preferred forms, the dispenser housing has an aperture located between the lamp and the in-use indicator surface so that light can pass directly to the exterior of the housing and onto the indicator surface which reflects the light. To achieve maximum visibility for the consumer, the indicator surface preferably projects as a lip or ledge out from the front end, opposite the plug end, and faces upwardly, preferably in the same direction as the volatiles are dispensed. Reflective surfacing or coating can be used to increase the illumination of the indicator. With the full length of the upper face of the indicator ledge illuminated, it is readily visible by a person standing near a wall mounted electrical outlet, which are conventionally located near the floor. The dispenser can be oriented in this position, in which the liquid container is upright and the indicator surface faces upward, whether the electrical receptacle has horizontally or vertically spaced openings. A special hold-down feature of the housing acts as a strain relief to limit pulling forces on, and movement of, electrical components (conductors, fuses, etc.) as the electrical plug is oriented or re-oriented during or after initial assembly.

Preferably, the lamp is a small LED providing long life and low power consumption. Regardless of type, the lamp is preferably kept separated from the heater by a dividing wall, preferably depending down from an upper part of the dispenser housing. The wall helps reduce heat-related wear on the lamp and also acts to redirect, by reflection, light that would otherwise pass to the interior of the housing toward the in-use indicator surface, thus increasing the intensity and efficiency of the illumination on the indicator surface.

In still other preferred forms, a thermal or current/voltage fuse is preferably mounted in-line with the heater to cut power and keep the device from overheating. The housing can have one or more holding areas, preferably including outwardly projecting grips located at cooler areas of the dispenser, such as opposite sides of the housing to lateral sides of the electrical plug. The housing can also have inwardly extending projections at the outlet opening. These features help make the dispenser more user friendly by reducing the likelihood of the user touching hot surfaces.

Preferably, the liquid volatiles are contained in a container, such as a threaded-necked bottle, with a wick having a submerged end and an opposite exposed end. The exposed end can be disposed in the center opening of a ring heater. Preferably, the open center of the heater has a sectional area no greater than that of the outlet opening. More preferably, the outlet opening is located near the heater, for example no more than 5 mm apart, with an air space therebetween. Still more preferably, the outlet opening is funnel shaped, with an outer opening and an inner opening sized smaller than the outer opening. The inner opening can be defined by an upturned lip, or inner peripheral wall, extending toward the outer opening, preferably angling in the direction from the inner opening to the outer opening and radially inwardly at an angle between 5 and 90 degrees from horizontal.

The dispenser breathes by routing air up from its underside around the liquid volatile container. Vertical ducts are provided around the container to better facilitate this. Air can then flow around the container and up along the wick and through the center of the ring heater. The cooler air moving from the bottom of the dispenser warms as it nears the heater and the lighter, warmer air, carrying the evaporated volatile, moves quickly up through the interior of the dispenser and out the outlet opening. The funneled configuration of the outlet opening, and particularly the upturned lip, helps create a plume of the volatile carrying air which rises up in a column above the dispenser before dispersing. Also, the outlet is located close to the heater and has an opening area that is the same as or larger than the open center of the heater so that most, if not all, of the volatile carrying air passes directly out of the outlet, rather than getting trapped inside the housing. The combined effect of the air routing as well as the outlet configuration and its relatively close spaced relation to the heater is more effective, wider dispersion of the active ingredient.

In another aspect, the present invention provides a plug-in dispenser of liquid volatiles of the type having a heater for evaporating liquid volatiles. The dispenser has a lamp interior to a housing of the dispenser which when energized transmits light to an exterior of the housing and incident with an exterior in-use indicator surface of the housing to illuminate the in-use indicator so it is readily visible from a viewing side of the dispenser.

In another aspect, the invention provides an electric liquid volatile dispenser having a housing which defines holding areas at opposite sides of the housing. The holding areas can include raised ribs extending out from the housing. The location and raised nature of the ribs make them cooler to touch than other places on the dispenser nearer the heater. And, the ribs present an intuitively apparent place to grasp the dispenser, particularly given their location at the lateral sides of the housing.

Another aspect of the invention pertains to the electrical plug being mountable to the housing in at least two angular orientations. The housing preferably defines a hold down for fixing the position of electrical components coupled to the plug, such as conductors and a power cut off fuse. This not only provides for strain relief of the conductor, but also maintains consistent spacing of the fuse from the heater, which is particularly important when a temperature cut off fuse is used to ensure that it trips when expected.

Still another aspect of the invention pertains to the outlet opening. In one form, the sectional area of the outlet opening is at least as large as that of the open center of the ring heater. In another form, the outlet opening defines a wall or baffle extending in a direction away from the heater that redirects ambient air away from the outlet opening. Both of these features work to better expel the volatized active from the dispenser housing, achieving both better overall dispersion of the active and reduced condensation inside and outside the housing.

Even more preferred forms provide for the outlet opening to be located directly above the wick, essentially disposed about an axis extending through the wick and the ring heater opening. The baffle can be oblique with respect to the extension of the wick, preferably angling inwardly and upwardly (away from the heater) at an angle between 5 and 90 degrees inclusive from horizontal. The baffle is also preferably arcuate, such as in a continuous or segmented frusto-conical form, defining an opening having a sectional area at least that of the heater opening. And, still more preferably, the outlet opening is recessed from a top side of the housing in a funnel shape defining an outer opening and an inner opening sized smaller than the outer opening.

These attributes of the outlet opening provide for better dispersion and cut down on condensation primarily by forming the active laden air into a column-like plume, which can rise above the dispenser before emanating through the ambient air. The column of air can pass straight up through the outlet opening without spreading out until after passing out of the dispenser. The outlet opening is sized to accommodate the plume of air without being so large that objects, especially fingers, are likely to fit down into the housing.

This brief summary of the invention has been provided so that the nature of the invention may be generally understood. However, this summary should not be construed to limit the invention. The foregoing and other objects, aspects, features and advantages of the present invention will become apparent from the following detailed description of the preferred embodiment taken in conjunction with the accompanying drawings.

DESCRIPTION OF THE PREFERRED EMBODIMENT

Figure 1:
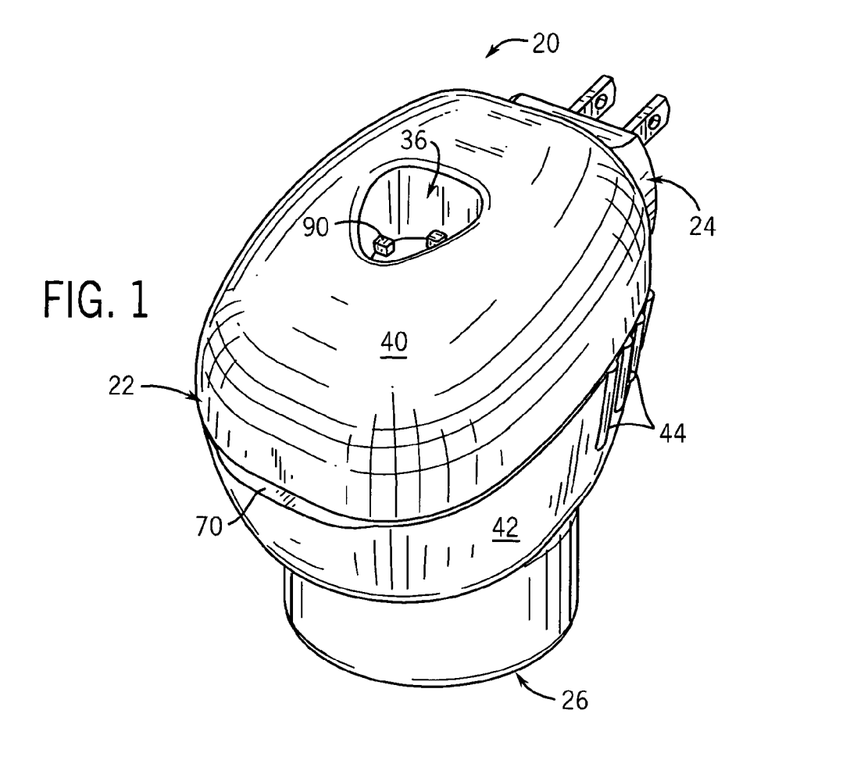
FIG. 1 is a perspective view of the electric volatile dispenser of the present invention.
Figure 2:
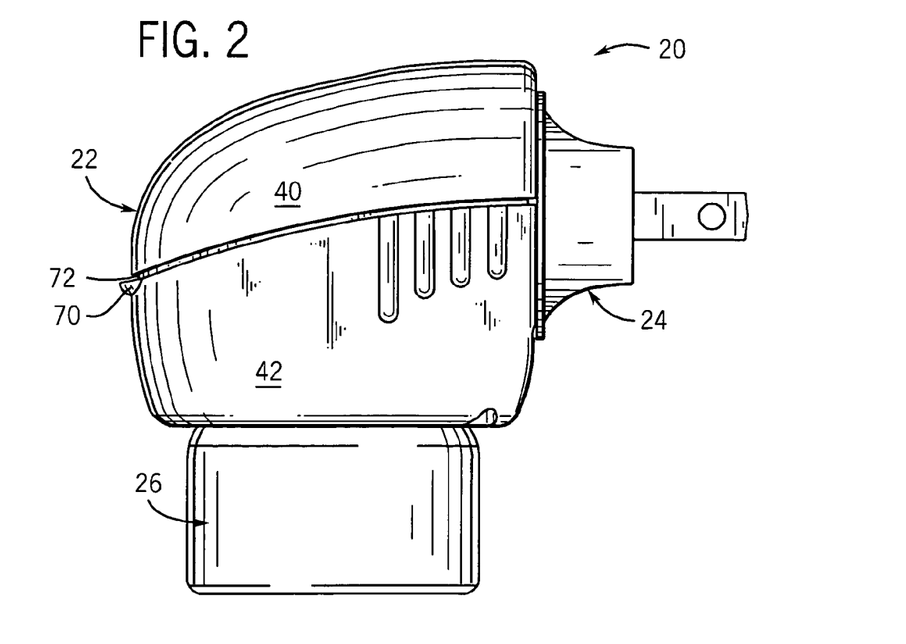
FIG. 2 is a side elevational view thereof.
Figure 3:
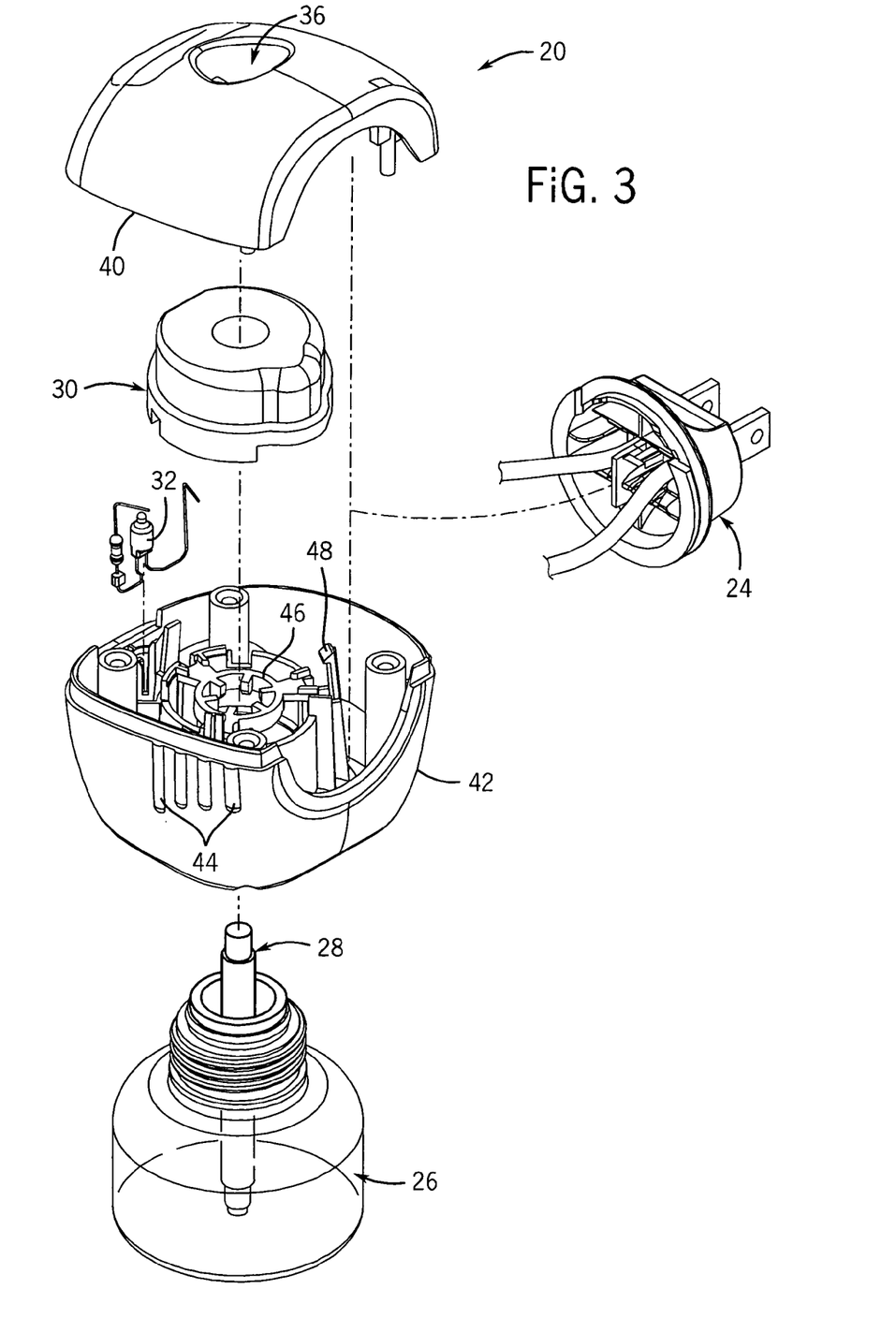
FIG. 3 is an exploded perspective view thereof.

FIGS. 1–3 illustrate a preferred embodiment of an electric volatile dispenser 20 according to the present invention. Generally, the dispenser 20 has a compact housing 22 mounting an electrical plug 24 at one end and a bottle of liquid volatiles 26 at its underside. The bottle of liquid volatiles 26 is enclosed except for a wick 28 which has one end submerged in the liquid inside the bottle and the other end extending to the outside of the bottle. The housing 22 contains a heater 30, an LED lamp 32 and a power-cut off fuse 34, all of which are electrically coupled to the plug 24 via conductor leads running from the metal prongs of the plug 24.

The liquid includes a heat activatable chemical ingredient, preferably an insecticide. However, various insect control chemicals, fragrances, disinfectants, sanitizing agents or other heat-activated chemicals can also be used. The bottle is preferably enclosed by a cap that is fit onto a threaded neck section which removably threads into a cavity at the underside of the housing 22. The cap has a centered opening that seals against the wick 28 and retains it in an upright position.

The wick 28 can be formed of any conventional materials, such as porous ceramics, bonded fibers, sintered plastics. The shaft of the wick can have a conductive and/or impermeable outer coating used to affect the rate of dispersion and to provide more uniform heat distribution. Suitable materials for the outer coating include plastics, paints, or various types of solid sleeving including aluminum, copper and high density/temperature plastics. U.S. Pat. No. 5,647,053 discloses such preferred wick constructions.

The heater 30 can also be any conventional heating device, however, preferably it contains a positive temperature coefficient ("PTC") thermistor which uses its inherent self-regulating material properties to maintain and an essentially constant temperature over a wide range of voltage and heat dissipation conditions. Such a PTC heater is preferably in a ring configuration with an open center in which the exposed portion of the wick 28 can fit to provide essentially uniform heating of the entire exposed portion of the wick 28. U.S. Pat. No. 6,411,776 discloses one such suitable PTC heater device. The heater should be able to provide generally consistent operating temperature sufficient to vaporize the liquid volatiles, which typically are selected to have activation temperatures between 80 and 150° C.

Should an excessive temperature or over-current/over-voltage situation occur, internal components of the heater could permanently or temporarily open the circuit to cut power to the heater. However, the present dispenser 20 preferably uses the aforementioned fuse 34, placed in series with the heater 30, to permanently open the heater circuit in the vent of an overload situation, and thereby disable the dispenser 20. The fuse 34 can either be a fusible resistor responsive to current and voltage or a thermal cut-off fuse responsive to temperature. Such thermal cut-off fuses are well known in the art, and U.S. Pat. No. 5,796,914 discloses their use for an electric fumigation device. The entire disclosure of this, and all of the aforementioned patents, are hereby incorporated by reference as though fully set forth herein.

Figure 9:
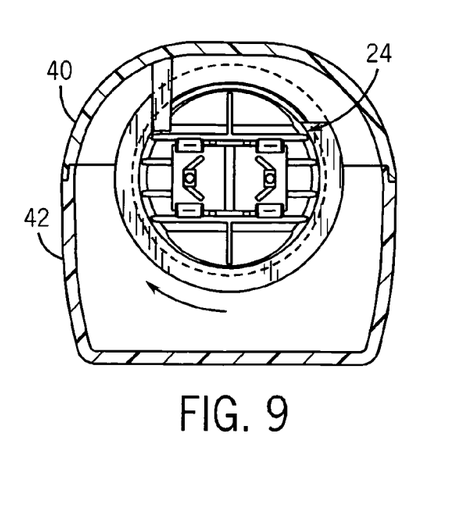
FIG. 9 is a sectional view taken along line 9—9 of FIG. 4 showing an electrical plug in a horizontal orientation.
Figure 10:
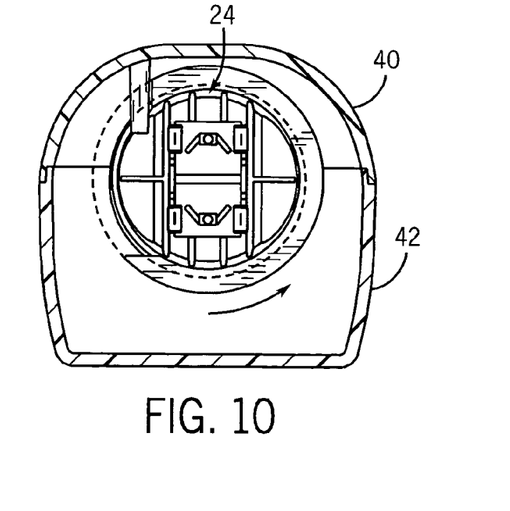
FIG. 10 is a view similar to FIG. 9 showing the plug rotated to a vertical orientation.

The heater 30 is coupled to power by the plug 24, which can have any prong configuration meeting the standard of the United States or any other country. As shown in FIGS. 9 and 10, the entire plug 24 unit can be mounted in the housing 22 in any angular orientation, however, it is preferably designed to mount in one of two orientations in which the prongs are either spaced apart horizontally or vertically. A circular end on the body of the plug 24 has a circumferential groove to facilitate such positioning.

Having described the basic features of the dispenser 20, its general operation will now be described briefly. With the plug 24 fit into a standard electrical receptacle (not shown), the heater 30 warms the air surrounding the exposed portion of the wick 28, and thus the wick 28 itself. Liquid volatile travels up the wick 28, by the force of capillary or "wicking" action, and volatizes as its temperature is elevated. The heated air also tends to create a chimney effect to draw the volatile containing air up through the housing 22 and expel it out through an outlet opening 36 at the top of the housing 22 so that the volatile can emanate through the room. While the heater 30 is energized, the lamp 32 is illuminated to indicate that the dispenser is activated. Depending on the type of fuse employed, the fuse 34 will open the circuit to the heater 28 in the event the operating temperature, current or voltage rises too high.

The dispenser 20 of the present invention thus operates in a manner similar to other such devices. However, it has several features which provide for improved functionality, particularly with regard to dispersion of the volatiles and user friendliness. Many of these features are afforded by the unique construction of the housing 22.

As shown in FIG. 3, the housing 22 is formed of upper 40 and lower 42 shells, preferably molded of a suitable plastic resin. The upper shell 40 overlaps the lower shell 42 at the seam (see e.g. FIG. 6), which helps keep liquids or other contaminants from falling into the housing 22. The sides of the lower shell 42 have a series of vertically spaced raised ribs 44 defining holding areas. Since the holding areas are spaced from the heater 30 and the ribs 44 project outward from the flat surfaces of the housing 22, they provide a cooler area for the user to grasp the dispenser 20, for example when unplugging it from the electrical receptacle. The arrangement and opposite side locations of the ribs 44 visually indicate to the user that the dispenser 20 should be handled in those areas. The user will likely intuitively grasp the dispenser 20 at the ribs 44, rather than at other warmer areas, and thus reduce the likelihood of encountering high temperatures.

Figure 7:
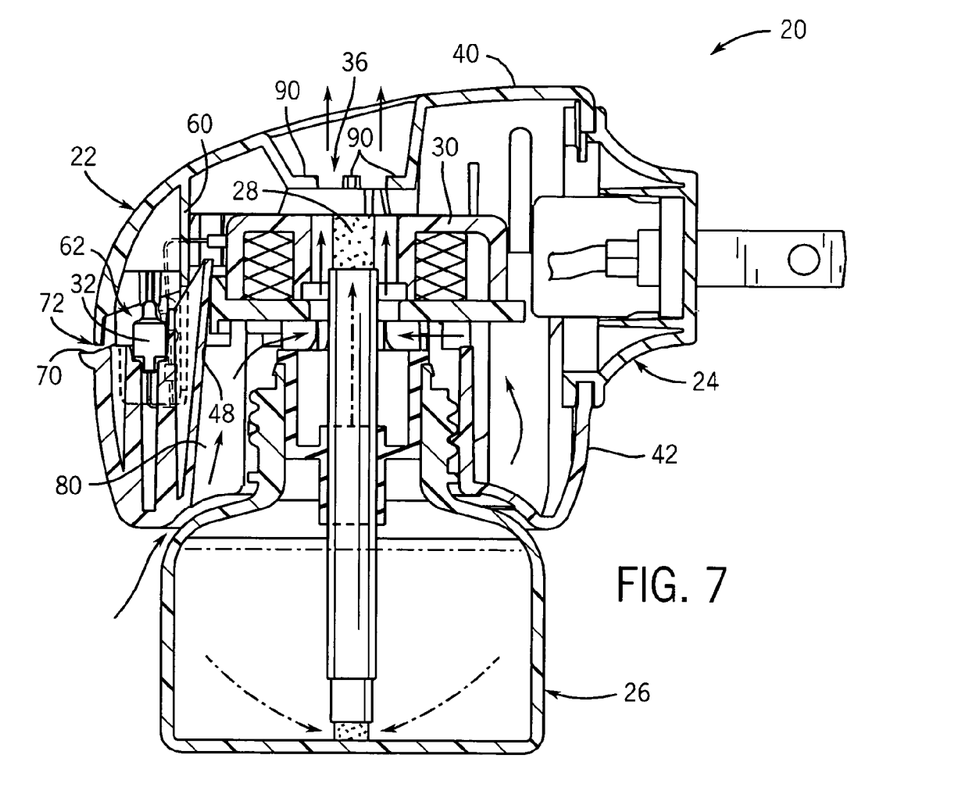
FIG. 7 is a side sectional view taken along line 7—7 of FIG. 4.

The inside of the housing 22 includes ribbing and other generally vertically extending structures used to connect the two shells and support the internal components, namely the heater 30, lamp 32 and fuse 34. As shown in FIG. 3, the lower shell 42 defines an annular support 46 on which the heater 30 sits. Spring clips 48 secure the heater 30 in place, as shown in FIG. 7. As shown in FIG. 7, the upper 40 and lower 42 shells also have opposing structures 50 and 52 that act as a hold-down and strain relief for the conductor to which the fuse 34 is connected. The lower structure 52 has a small groove or notch 54 at its upper end that receives the conductor and the upper structure 50 clamps down on the conductor slightly to fix its position and also take up pulling forces on the conductor. This is particularly useful when the orientation of the plug 24 is being set or changed. Preferably, the conductor is clamped adjacent the fuse 34 to fix its position. This is important when the fuse 34 is a temperature cut-off type fuse so that during assembly the fuse maintains a consistent distance from the heater. This helps ensure that the fuse will realize relatively consistent temperatures during normal operation, and thus trip only when an actual over-temperature condition arises. If the fuse is too close to the heater, it may trip the circuit before the maximum temperature was reached, and conversely, if it is too far from the heater it may not trip when needed.

The upper 40 shell also has downwardly extending interior walls 60 that define a light chamber 62 at the end of the housing 22 opposite the plug 24. These walls provide a number of benefits. Specifically, they assist in positioning the lamp 32, thereby providing consistently located illumination. They shield the lamp 32 from the heater 30, thereby reducing heat-related aging. And, they reflect light that would otherwise be lost inside the housing 22, to the outside of the housing 22 where it can be seen by the user.

In particular, the light is directed onto a special in-use indicator 70, which provides the user indication that the dispenser 20 is active. This in-use indicator 70 is a substantially flat or, alternatively, a convexly or concavely curved, upward facing exterior surface of the housing 22 that projects out from the end of the housing lower shell 42 opposite the plug 24 to form a lip or ledge structure. The upward facing surface is located adjacent to a very narrow lateral slit or aperture 72 (see FIG. 7) between the housing shells. The aperture 72 permits light from the lamp 32 to be transmitted unobstructed to outside the housing 22 and reflected off of the exterior surface of the in-use indicator 70. The illumination of the rather broad exterior in-use indicator 70 provides a highly visible notification to the user that the dispenser 20 is on. Because the aperture 72 is narrow and is located at a vertical end of the housing 22 (rather than at the top) there is less opportunity for items to enter into the housing 22.

Since the lamp 32 is coupled to the plug 24 in series with the heater 30, it will illuminate only when the heater 30 is active. This can be helpful at initial start-up so that the user knows the device is working as the heater is warming to operating temperature before the volatile is activated. This can prevent the user from incorrectly believing that the dispenser is defective. It can also remind them to unplug the dispenser after the volatiles have been exhausted to avoid unnecessarily energizing the heater. It also warns the user that there may be hot surfaces to avoid.

Figure 4:
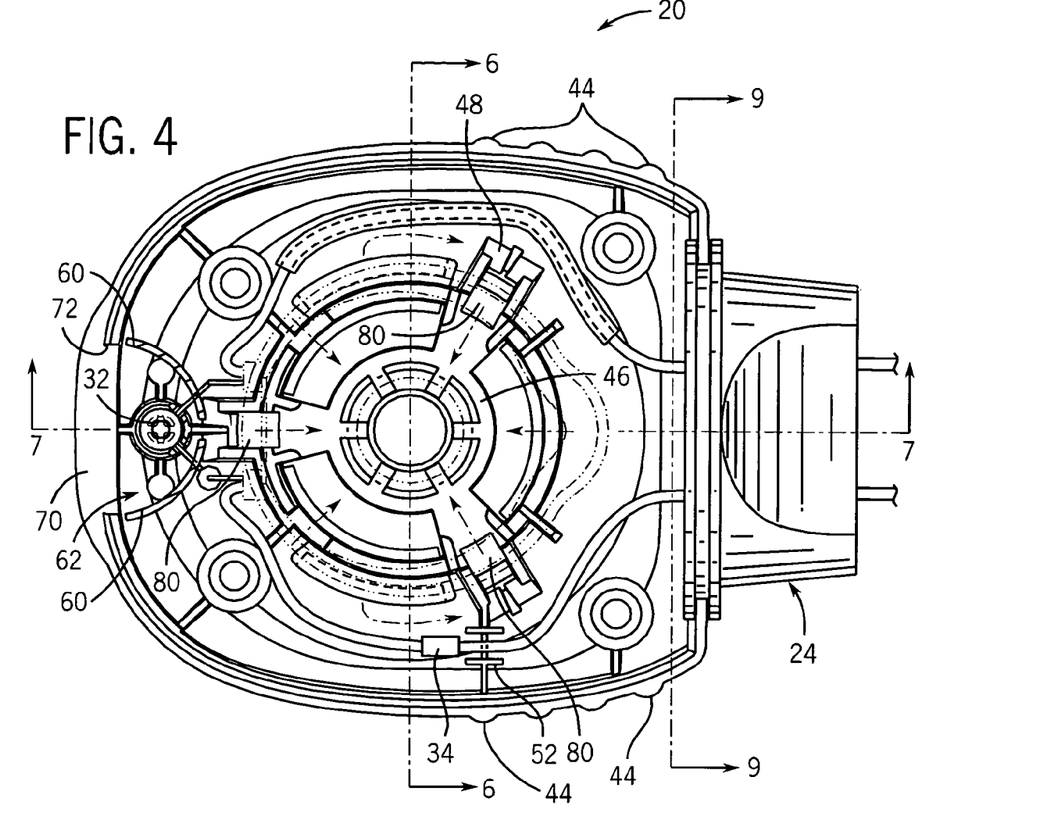
FIG. 4 is a view looking down from the inside of the dispenser.
Figure 5:
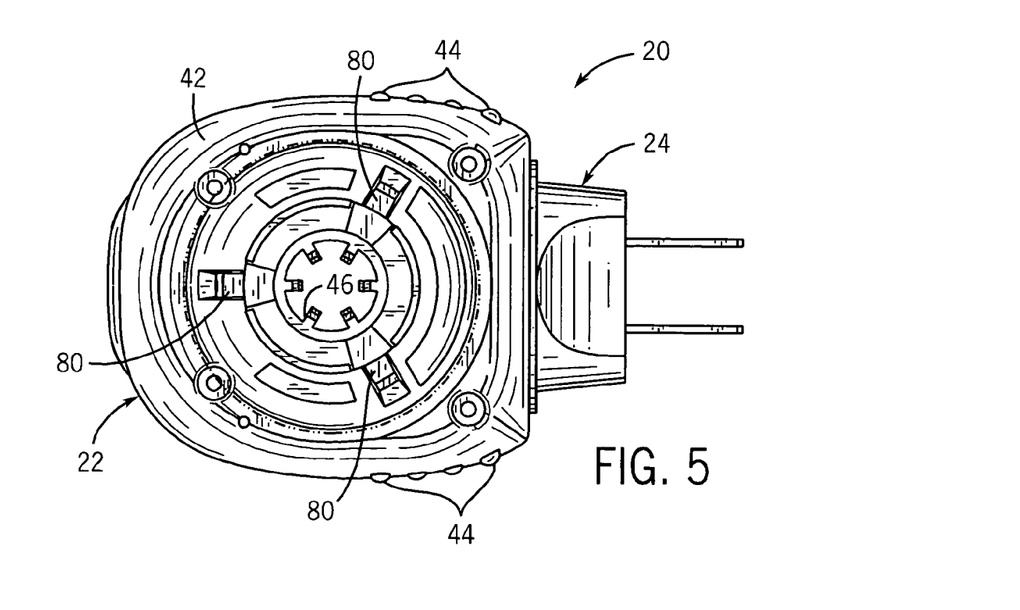
FIG. 5 is bottom plan view of the dispense without the liquid volatile container shown.
Figure 6:
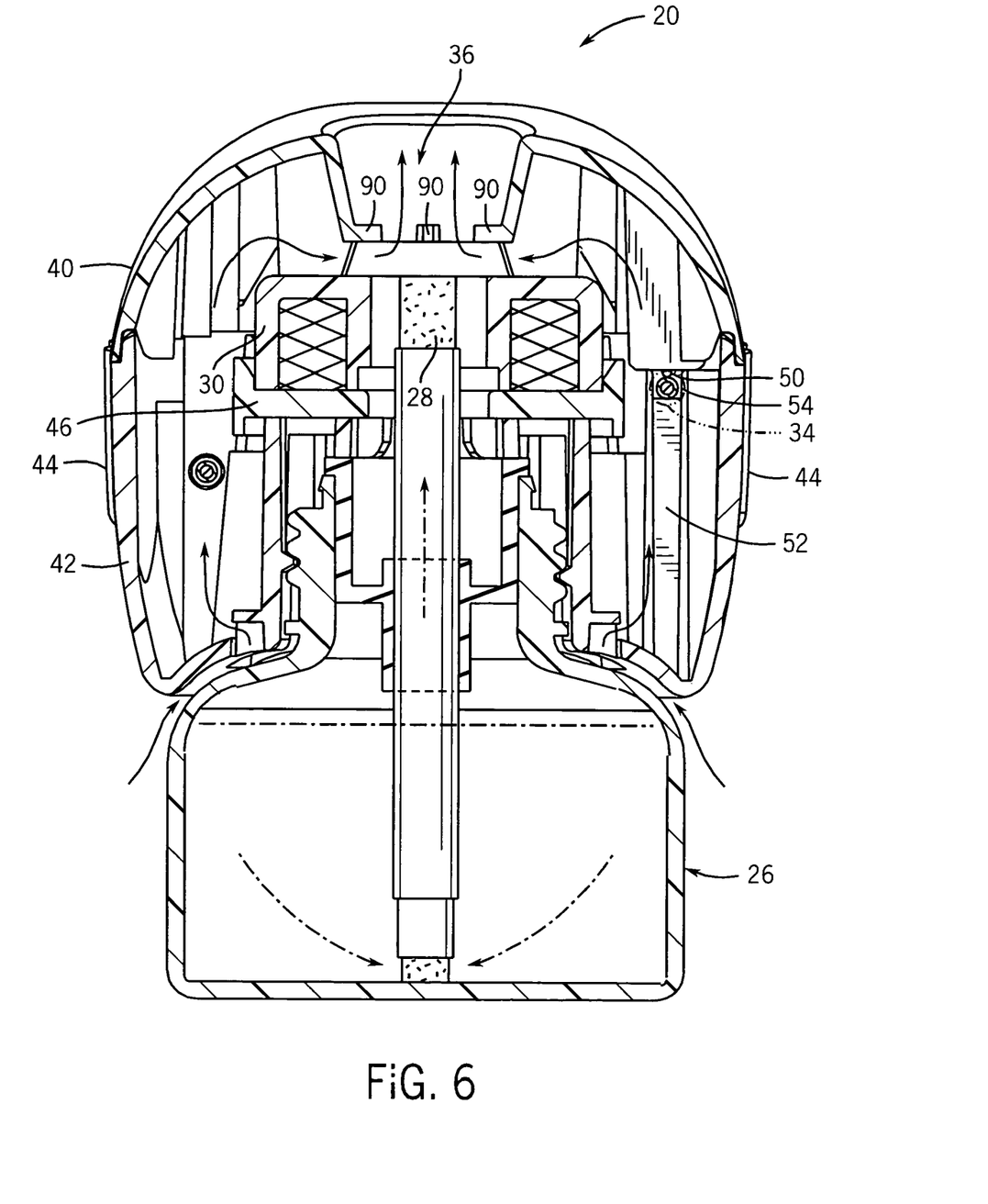
FIG. 6 is an end sectional view taken along line 6—6 of FIG. 4.

As mentioned, the dispenser 20 has several features which provide for more effective dispersion of the volatile materials. Referring to FIGS. 4–6, the lower shell 42 of the housing 22 forms three vertical channels or air ducts 80 spaced around and opening at the cavity where the bottle of volatiles 26 mounts to the housing 22. When the bottle of volatiles 26 is fully mounted into the housing 22 as shown in FIGS. 6 and 7, a small air gap exists between the upper part of the bottle and the housing 22 so that air can flow into the vertical air ducts 80. The air ducts 80 carry the air up into the housing along side the neck of the bottle. From there, the air can flow up and inwardly alongside the exposed part of the wick 28, through the center of the heater 30 and then on through the outlet opening 36. The air ducts 80 thus provide for more flow volume and allow air to flow alongside the wick where it can pick up the volatile and carry it up through the outlet opening 36.

As shown in FIGS. 1 and 6–8, the outlet opening 36 is located at the top of the housing upper shell 40 directly (vertically) above the wick 28 and the center opening of the heater 30. The outlet opening 36 is defined by a somewhat funnel-shaped recessed inner wall effectively defining an inner opening and a larger outer (or upper) opening. Four small prongs 90 extend radially inward at the lower part of the opening sufficient to keep a finger from contacting the heater 30. The sectional area of the outlet opening 36 is the smallest at the bottom. The minimum sectional area of the outlet opening 36 is designed to be at least that of the center opening of the heater 30, and as mentioned, to be vertically aligned therewith. This helps ensure that the warm, volatile laden air rising from around the wick 28 passes out of the housing 22 without being trapped under the upper shell 40, which could unduly heat the housing 22 or cause condensation inside the housing 22. In the embodiment shown with the prongs 90, the bottom of the outlet opening 36 is actually sized larger than that at the center of the heater 30, to accommodate the space occupied by the prongs 90, however, the overall sectional area of the outlet opening 36 is at least that of the heater opening. In one preferred embodiment, the heater opening is about 1 centimeter ("cm") in diameter, and the outlet opening is about 1.2 cm across at the bottom, with the distance between opposite prongs being about 0.8 cm. Also, it is important for the bottom of the outlet opening 36 to be spaced somewhat from the top of the heater 30. This is to allow air flow therebetween (see FIG. 6) to aid in dispersion as well as to keep the upper shell 40 from realizing excessively high temperatures, which in this case is preferably no more than 80° C. A distance of less than 10 mm is likely to be sufficient for most suitable PTC heaters, preferably it is no more than 5 mm, and even more preferably it is about 3 mm.

Figure 8:
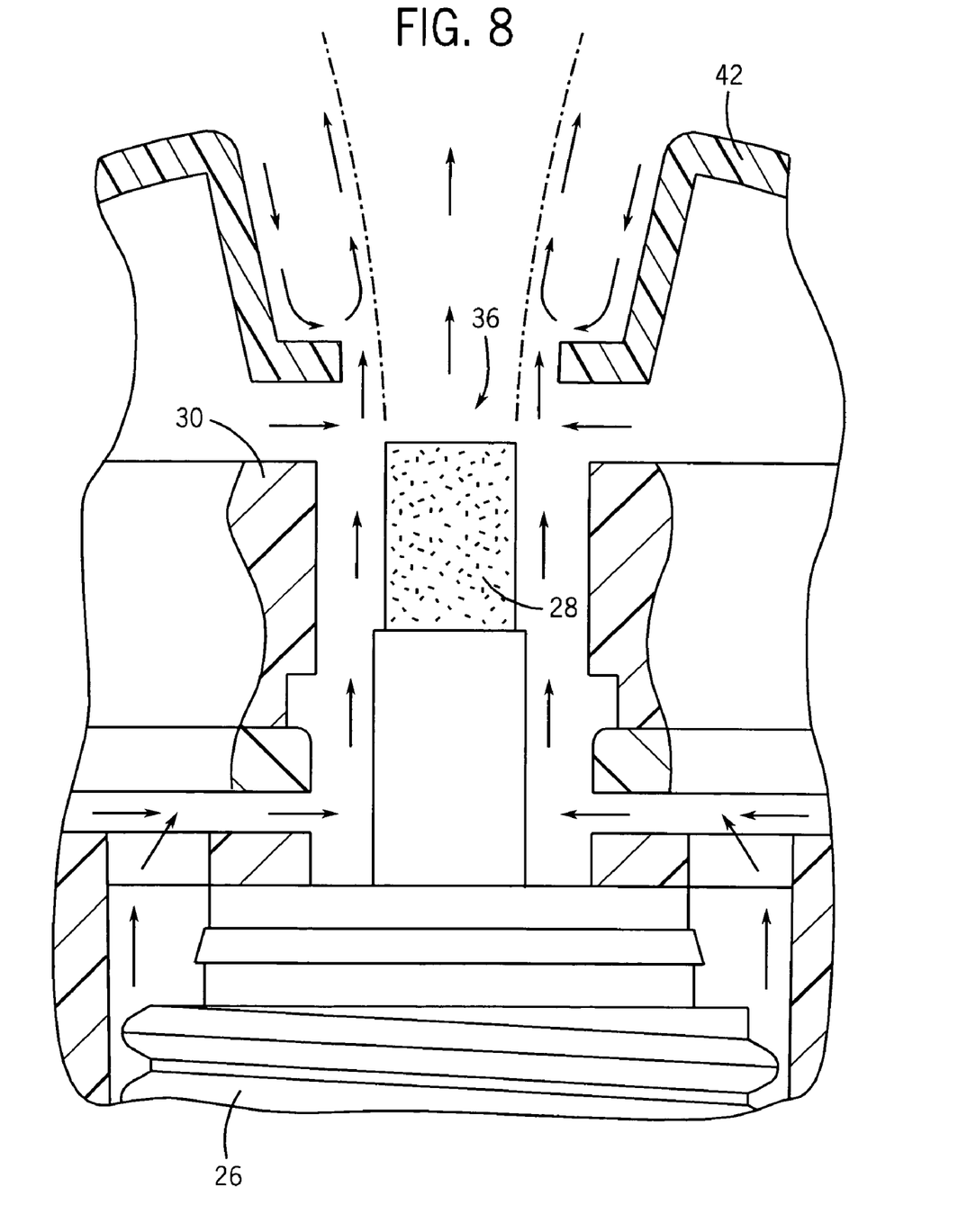
FIG. 8 is an enlarged partial sectional view illustrating the air flow pattern around the wick and outlet areas of the dispenser.

As shown in FIG. 8, the configuration, sizing and spacing of the outlet opening 36 and heater/wick arrangement (along with the air ducts 80) provides for improved dispersion of the volatized actives. Air flow rising from the bottom of the dispenser up through the housing 22 will flow up along the wick 28 through the center of the heater 30 as well as around and above the heater 30. This will effect a primarily upward and inward air flow pattern tending to centralize and elevate the warm active laden air up through the outlet opening 36. The column-like plume of air passing through the outlet opening 36 will encounter about its periphery cooler ambient air that makes its way around the funneled contour of the outlet opening 36 before being turned back generally in the direction it came by the force of the plume of exiting air. This helps to extend the column like flow pattern to above the dispenser, thereby creating a more forceful and elevated volatized air stream, and thus more effective dispersion of the actives.

Depending on the concentration and type of active material being dispensed, it is possible for a small amount of volatized active to condense at the exterior of the housing, particularly along the upper edge of the outlet opening. This can leave a powdery residue build up on the outside of the housing at or around the outlet opening, which can discolor the housing and be contacted by the user.

Figure 11:
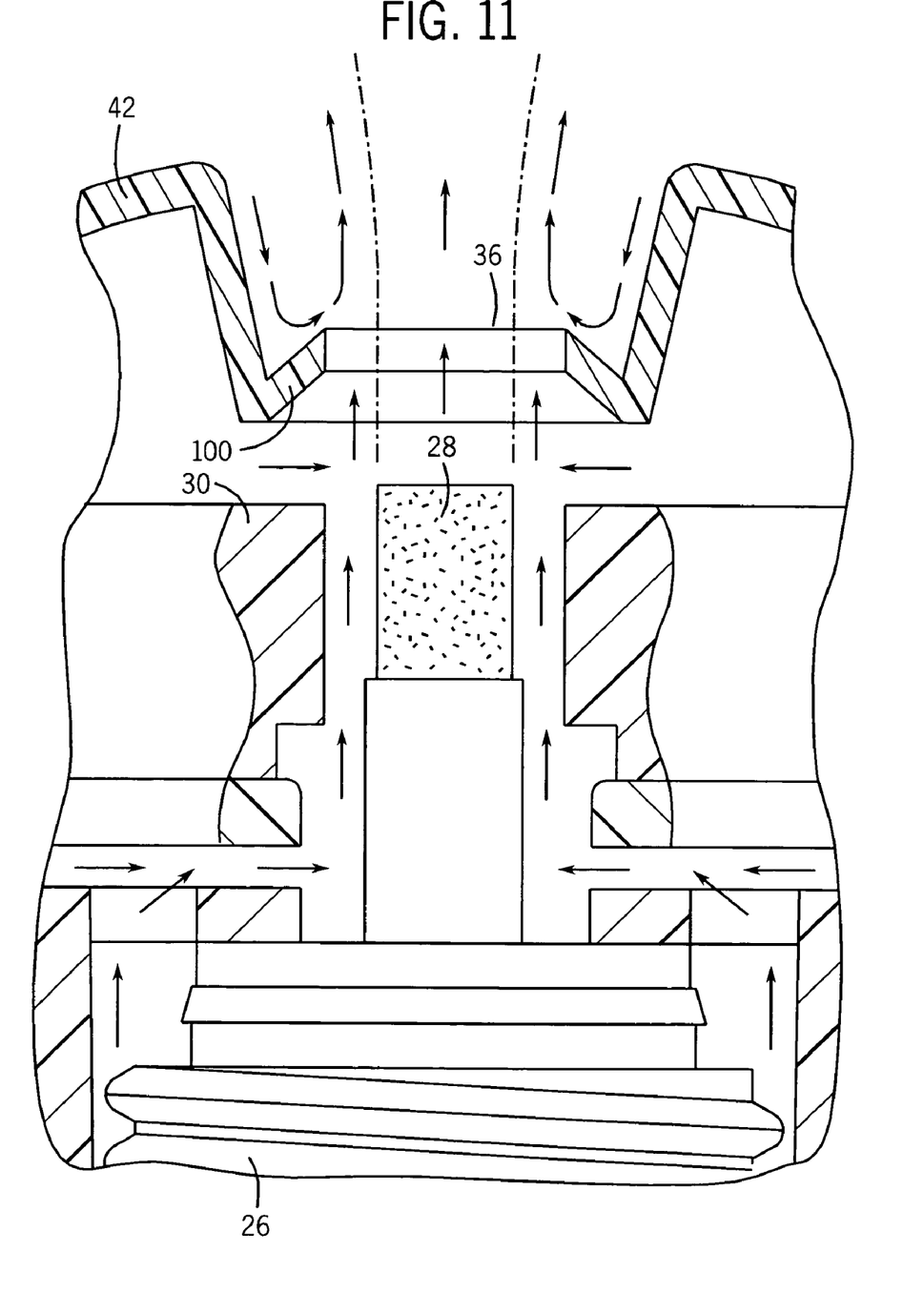
FIG. 11 is a view similar to FIG. 8 albeit with an angled wall at the outlet opening.

As shown in FIG. 11, to avoid this, the outlet opening can be formed with a frusto-conical wall or baffle 100 disposed about an axis passing through the length of the wick and tapering radial inward and upward away from the heater. This baffle 100 further enhances the vertical component of the expelled air stream by more effectively re-directing the ambient air passing down into the funnel of the outlet opening 36. As shown by the arrows in FIG. 11, the turned back ambient air tends to concentrate the expelled air to form an even more forceful column-like plume of air able to rise even higher above the dispenser. Empirical data indicates that the presence of the angled baffle 100 essentially eliminates any condensation or particulate deposit of the volatized active on the outside (or inside) of the housing.

In the depicted embodiment, the baffle 100 extends about 45 degrees from horizontal. However, this can vary depending on the application, for example an angle between 5 and 90 degrees from horizontal is envisioned to be suitable to achieve the desired effect in most circumstances. The angled baffle 100 could be segmented, rather than continuous through 360 degrees. Also, like before, preferably a minimum outlet opening size is maintained at or greater than the opening of the heater, and small radially inwardly extending prongs can be added to keep out fingers and the like.

Although a specific embodiment of the present invention has been described in detail, it will be understood that this description is merely for purposes of illustration. Various modifications of, and equivalent structures corresponding to, the disclosed aspects of the preferred embodiment in addition to those described above may be made by those skilled in the art without departing from the spirit of the following claims. Accordingly, the scope of the invention defined by the following claims should be accorded the broadest reasonable interpretation so as to encompass such modifications and equivalent structures.

INDUSTRIAL APPLICABILITY

The invention provides an electric dispenser of volatile liquids, such as insecticides, fragrants and the like, with improved volatile dispersion characteristics and in-use indication.

We claim:

1. An electrically activated dispenser of liquid volatiles, comprising:
   a housing having an outlet opening and an exterior in-use indicator surface;
   a heater mounted in the housing;
   an electrical plug electrically coupled to the heater;
   means for mounting a container of liquid volatiles to the housing proximate the heater to permit evaporation of the liquid volatiles through the outlet opening; and
   a lamp mounted in the housing for transmitting light exterior to the housing to reflect from the in-use indicator surface;
   wherein the in-use indicator surface projects out from the housing to form a ledge.

2. The dispenser of claim 1, wherein the housing further includes an aperture between the lamp and the in-use indicator surface.

3. The dispenser of claim 1, wherein the in-use indicator surface faces a side of the housing at which the outlet opening opens.

4. The dispenser of claim 1, wherein the in-use indictor surface is located at a side of the housing opposite the electrical plug.

5. The dispenser of claim 4, wherein the in-use indicator faces upwardly when the electrical plug is received in an electrical outlet.

6. The dispenser of claim 1, wherein the lamp is an LED.

7. The dispenser of claim 1, wherein a wall is disposed between the lamp and the heater.

8. The dispenser of claim 7, wherein the wall is a part of the housing.

9. The dispenser of claim 7, wherein the housing has an aperture between the lamp and the in-use indicator surface and wherein the wall redirects light from the lamp through the aperture.

10. The dispenser of claim 1, further comprising a container of liquid volatiles having a wick with one end submerged in the liquid volatiles.

11. The dispenser of claim 10, wherein the container includes a wick with one end submerged in the liquid volatiles and an opposite end disposed at the open center of the heater.

12. The dispenser of claim 1, further including a fuse electrically coupled between the heater and the electrical plug.

13. The dispenser of claim 1, wherein the housing defines inwardly extending projections at the outlet opening.

14. The dispenser of claim 1, wherein the heater is a ring heater with an open center having a sectional area no greater than that of the outlet opening.

15. The dispenser of claim 1, wherein the outlet opening has an outer opening and an inner opening, the inner opening being sized smaller than the outer opening.

16. The dispenser of claim 15, wherein the inner opening is defined by an inner wall extending toward the outer opening.

17. The dispenser of claim 16, wherein the inner wall angles in the direction from the inner opening to the outer opening.

18. The dispenser of claim 17, wherein the inner wall extends inwardly at an angle between 5 and 90 degrees from horizontal.

19. The dispenser of claim 1, wherein the outlet opening is located proximate the heater with an air space there between.

20. The dispenser of claim 19, wherein the outlet opening is no more than 5 mm apart from the heater.

21. The dispenser of claim 1, wherein the housing has two parts, with an upper part overlapping a lower part.

22. The dispenser of claim 1, wherein the housing defines an air duct proximate the container to allow air to pass between the container and the housing.

23. The dispenser of claim 1, wherein the dispenser is a plug-in dispenser of liquid volatiles where the lamp, when energized, can illuminate the in-use indicator so it is readily visible from a viewing side of the dispenser.

24. The dispenser of claim 1, wherein the housing defines holding areas at opposite sides of the housing; and
   a container of liquid volatiles is mounted to the housing proximate the heater to permit evaporation of the liquid volatiles through the outlet opening.

25. The dispenser of claim 24, wherein the holding areas include raised ribs extending out from the housing.

26. The dispenser of claim 1, wherein the electrical plug is electrically coupled to the heater by an electrical conductor and mountable to the housing in at least two angular orientations;
   there is also a container of liquid volatiles mountable to the housing proximate the heater to permit evaporation of the liquid volatiles through the outlet opening; and
   the housing further defines a hold down for fixing the position of the electrical conductor.

27. The dispenser of claim 26, further including a power cut off fuse electrically coupled to the heater and wherein the hold down fixes the position of the fuse.

28. A plug-in dispenser of liquid volatiles of the type having a heater for evaporating liquid volatiles, the dispenser having a lamp interior to a housing of the dispenser which when energized transmits light to an exterior of the housing and incident with an exterior in-use indicator surface of the housing to illuminate the in-use indicator so it is readily visible from a viewing side of the dispenser;
   wherein the housing further includes an aperture between the lamp and the in-use indicator surface; and wherein the in-use indicator surface projects out from the housing to form a ledge.

29. The dispenser of claim 28, wherein the housing defines a divider wall between the lamp and the heater which reflects light from the lamp through the aperture and onto the in-use indicator surface.

30. An electrically activated dispenser of liquid volatiles, comprising:
- means to mount a container of liquid volatiles having a wick with an exposed end and an end submerged in the liquid volatiles;
- a heater positionable near the exposed end of the wick of a container so mounted; and
- a housing that receives a container so mounted and in which the heater is mounted, the housing having an outlet opening for expelling the volatiles from the wick;
- wherein the outlet opening is in the form of a downwardly narrowing funnel which has adjacent its lower end a radially inwardly and upwardly extending baffle configured such that ambient air traveling downward along the narrowing funnel will be redirected upward by the baffle and prevented from entering the housing through the outlet opening when liquid volatile is being dispensed from the dispenser.

31. The dispenser of claim 30, wherein the baffle is obliquely angled relative to the extension of the wick.

32. The dispenser of claim 30, wherein the baffle is an extension of the funnel.

33. The dispenser of claim 30, wherein the baffle angles inwardly at an angle between 5 and 90 degrees inclusive from horizontal.

34. The dispenser of claim 30, wherein the baffle is arcuate.

35. The dispenser of claim 30, wherein the baffle is frusto-conical.

36. The dispenser of claim 30, wherein the baffle defines an opening sized at least as large as an opening in the heater.

37. The dispenser of claim 30, wherein the outlet opening is located about an axis passing through the wick.

38. The dispenser of claim 37, wherein the heater forms a ring with an opening concentric with the axis.

39. The dispenser of claim 38, wherein the exposed end of the wick is at least partially disposed within the opening of the heater.

40. The dispenser of claim 38, wherein the baffle is conical defining an opening sized at least as large in sectional area as the heater opening.

41. The dispenser of claim 37, wherein the baffle is arcuate and angled obliquely with respect to the axis.

42. The dispenser of claim 37, wherein the outlet opening is recessed from a top side of the housing.

43. The dispenser of claim 30, wherein the outlet opening defines an outer opening and an inner opening sized smaller than the outer opening.

44. The dispenser of claim 43, wherein the baffle defines the inner opening.

45. The dispenser of claim 44, wherein the heater is a ring-shaped having an opening sized no greater than the inner opening of the outlet opening.

46. The dispenser of claim 45, wherein the inner opening and the heater opening are disposed about an axis of the wick.

* * * * *